United States Patent [19]

Lundstrom

[11] 4,180,331
[45] Dec. 25, 1979

[54] METHOD AND APPARATUS FOR SAMPLING AND MEASURING A CHARACTERISTIC OF FLOWING GRANULAR MATERIAL

[75] Inventor: John W. Lundstrom, Glendora, Calif.

[73] Assignee: Bindicator Company, Port Huron, Mich.

[21] Appl. No.: 678,149

[22] Filed: Apr. 19, 1976

[51] Int. Cl.² .................. G01N 21/48; G01N 1/00; G01N 21/26
[52] U.S. Cl. .................................. 356/445; 356/38; 250/576; 250/574
[58] Field of Search ............... 356/209, 210, 211, 212, 356/181, 38, 208; 73/73; 324/65 R; 116/117 C; 250/339, 573, 576, 319, 574; 350/188

[56] References Cited

U.S. PATENT DOCUMENTS

| 3,430,606 | 3/1969 | Pease et al. | 250/209 X |
|---|---|---|---|
| 3,665,201 | 5/1972 | Shea et al. | 250/574 |
| 3,714,444 | 7/1973 | Carr et al. | 356/208 |
| 3,776,642 | 12/1973 | Anson | 356/212 X |
| 3,818,333 | 6/1974 | Walker | 324/58.5 A |
| 3,903,877 | 9/1975 | Terada | 350/63 |
| 4,024,407 | 5/1977 | Meric et al. | 250/574 |

*Primary Examiner*—Vincent P. McGraw
*Assistant Examiner*—Rodney Bovernick
*Attorney, Agent, or Firm*—Barnes, Kisselle, Raisch & Choate

[57] ABSTRACT

A method and apparatus for sampling and optically measuring a selected characteristic of flowing granular material in which an optical window located at one end of a hollow sight tube is disposed in the material stream at an angle with respect thereto. A dam is carried by the sight tube downstream of the window to retard material flow and cause material to collect on the window surface. The selected material characteristic may then be measured as a function of an optical characteristic of the material as viewed through the sight tube and window. An air nozzle is disposed adjacent the window to remove the collected material sample at the end of a measurement sequence.

12 Claims, 4 Drawing Figures

METHOD AND APPARATUS FOR SAMPLING AND MEASURING A CHARACTERISTIC OF FLOWING GRANULAR MATERIAL

The present invention relates to optical test equipment and methods, and, more particularly, to instruments and methods for measuring a preselected characteristic of granular material, such as the moisture content thereof, using optical absorption/reflection techniques.

Prior art techniques of the above-described type may be generally classified in two distinct groups: those in which a sample is physically removed from the material bulk and tested at a remote location, and those which measure material characteristics without physically removing a material sample. Typical instruments of the former group are shown in U.S. Pat. Nos. 3,776,642 and 3,861,788. Material samples for such instruments may be hand-taken by a technician, a process which is obviously expensive, time consuming and subject to variations in sampling technique, or taken by relatively complex and expensive mechanical apparatus disposed in the material path, such as the apparatus disclosed in U.S. Pat. Nos. 3,575,055 or 3,802,270 for example. In either case, the material sample is either separately returned to the bulk or, more often, merely discarded.

Apparatus heretofore marketed by applicant's assignee under the trademark "Moisture Ray" epitomizes instruments and techniques of the second above-described group. In such instruments, a clear aperture, termed a sight window, is disposed adjacent the material path, as in the side wall of a holding bin or conveyor, so that electromagnetic radiation may be directed from externally of the window onto the material as the latter flows past the window. However, in techniques of this group the material must either be static, as in a holding bin, or, if dynamic, must flow past the window in a manner which insures that the window is always covered. Thus, separate drop chutes or bypass conveyors are usually provided in dynamic measurment applications. Other measuring techniques and apparatus of the second group are disclosed in U.S. Pat. Nos. 2,659,860 and 3,791,744.

It is a general object of the present invention to provide a method and apparatus for use in optically measuring selected characteristics of flowing granular material which obviate some or, preferably, all of the above-described disadvantages associated with and inherent in prior art techniques.

More specifically, it is an object of the present invention to provide a material sampling method and apparatus for use with conventional measuring equipment in which a material sample within a flowing stream is taken and held for a measurement operation without physically removing the sample from the flow path, and/or which quickly and economically returns the material sample to the flowing bulk.

It is a further object of the invention to provide a material sampling method and apparatus which is readily adaptable for use in existing conveyor installations and/or which isolates the measurement process from the effects of detrimental ambient conditions, such as dust and humidity.

The novel features which are considered to be characteristic of the present invention are set forth in particular in the appended claims. The invention itself, however, together with additional objects, features and advantages thereof, may be best understood from the following description when read in conjunction with the accompanying drawings in which:

Figure 1:
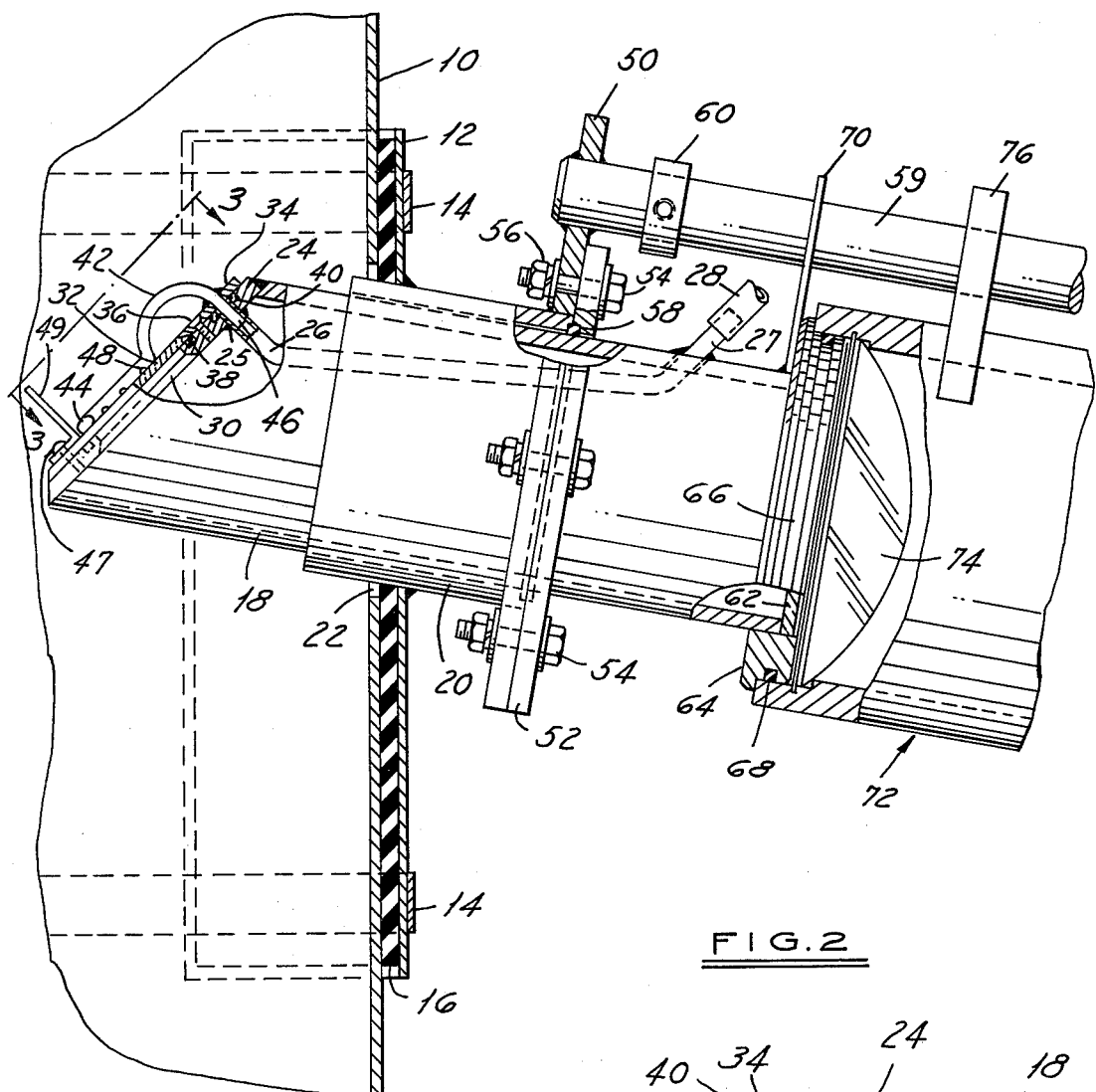
FIG. 1 is an elevational, partially sectioned view of a presently preferred embodiment of the invention.

Referring to the drawings, the depicted embodiment of the present invention comprises a semi-cylindrical mounting bracket or sleeve 12 secured by strap clamps 14 to a vertical material conveyor or chute 10 with a sealing gasket 16 squeezed between sleeve 12 and the conveyor wall. A hollow cylindrical sight tube 18 is slidably received within a gland 20 and extends through an opening 22 in chute 10. Gland 20 is fixedly carried by sleeve 12 such that the axis of sight tube 18 is oriented at an angle of about ten degrees with respect to the horizontal axis as viewed in FIGS. 1 and 4. Sight tube 18 terminated interiorly of chute 10 in an end cap 24 welded or otherwise fixedly attached to the rim of the end opendng of tube 18 at an angle of thirty-five degrees with respect to the tube axis. A metallic air line 26 enters tube 18 outwardly of gland 20 and runs the length of the sight tube to terminate at an opening 25 in end cap 24. Preferably, sight tube 18, end cap 24 and air line 26 are fabricated of similar metals, such as aluminum, and welded into an integral sub-assembly. The outer exterior end 27 of air line 26 projects radially beyond the wall of sight tube 18 and may be connected by a suitable conduit 28 to a source of compressed air (not shown), the purpose of which will be explained hereinafter.

End cap 24 has a central opening 30 over which a circular glass plate or window 32 is located and carried by an apertured window plate 34. Plate 34 is mounted to end cap 24 by screws 36. Window 32 has an outwardly tapering frustoconical side edge 33 (FIG. 2) which is engaged by a corresponding inner edge of plate 34. Where the material whose characteristic is to be measured is of the type which tends to pick up a charge of static electricity during material flow, the outer surface of window 32, as well as the tapering side edge thereof, is preferably coated with a thin layer of vapor-deposited conductive material. The conductive layer should be of a translucent material, such as tin. The coated window surface is connected to electrical ground (chute 10) through plate 34, cap 24, tube 18 and gland 20 to dissipate any static charge, and to thus prevent static material cling on the window.

Figure 2:
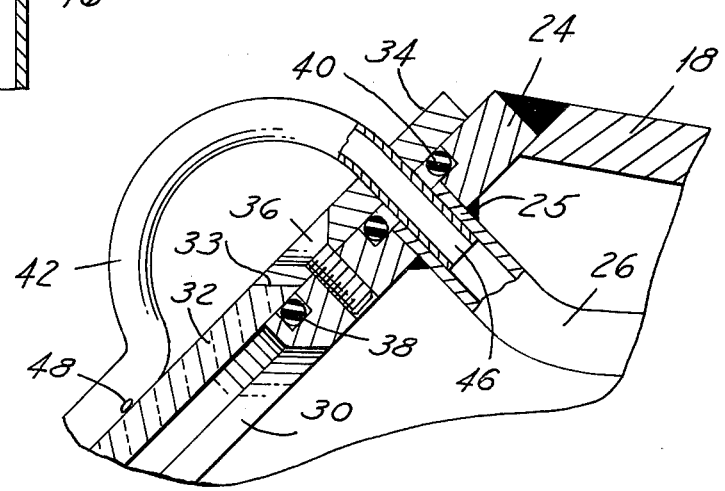
FIG. 2 is an enlarged fragmentary sectional view of a portion of the embodiment shown in FIG. 1.
Figure 3:
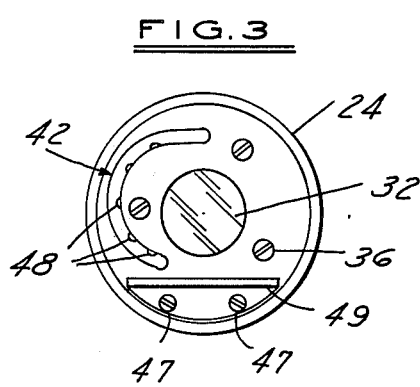
FIG. 3 is a veiw taken along the line 3—3 of FIG. 1.

An annular resilient seal 38 is captured in a corresponding groove in end cap 24 in sealing engagement with the axially inner face of window 32. A second resilient O-ring seal 40 is disposed in an end-cap recess about the open end 25 of air line 26, and is captured therein in sealing engagement with the axially inner face of lend plate 34. An air nozzle 42 is carried by plate 34 and has a closed outer end 44. The inner end 46 of nozzle 42 extends through a corresponding sealed opening in plate 34 to be telescopically received within the outer end of air line 26 as best seen in FIG. 2. Nozzle 42 is formed in an arc or semicircle about window 32, as best seen in FIG. 3, and has a plurality of inwardly directed radial openings 48 provided therein. An L-shaped bracket 49 is fastened to lens plate 34 by screws 47 and forms a material dam below window 32.

Gland 20 has a flange 50 extending radially therefrom. An annular plate 52 is mounted by bolts 54 and nuts 56 to flange 50, and cooperates therewith to capture a resilient O-ring 58 which forms a sealed bearing surface for sight tube 18. An adjustment rod 59 extends from flange 50 and has an adjustable stop 60 carried thereon. Sight tube 18 terminates at its outer end in a sealed glass window 62. An annular collar 64 is fitted about the outer end of sight tube 18 and has formed therein a radially outwardly facing groove 66 in which a resilient seal 68 is disposed. A guide plate 70 is affixed to tube 18 and is slidably received over rod 58.

An optical instrument case or head 72 is fitted over collar 64 in engagement with seal 68. Head 72 may include suitable elements, such as a light source and a photocell, for affecting the desired material characteristic measurement, and hence the components housed therein do not per se constitute part of the present invention. The head 72 shown for illustration in the drawings is that used in the above-referenced "Moisture Ray" measuring system. Briefly described, the "Moisture Ray" unit measures the moisture content of granular materials using a reflection/absorption measuring technique. A stabilized source (not shown) of near-infrared light emits energy which is focused by a lens 74 onto the material at the remote, material-collecting surface of window 32. Light reflected by the material is collected by lens 74 and directed onto a lead-sulphide photocell (not shown). A pair of narrow band interference filters (not shown) are alternately passed through the reflected beam so that the cell is alternately supplied with energy of a selected first wavelength sensitive to material moisture content and a second selected wavelength sensitive to material reflectivity but independent of moisture content. Head 72 may be connected to appropriate electronic circuitry (not shown) to separate and compare the two signals, and thereby yield an accurate indication of material moisture.

It has heretofore been found that measurement accuracy in enhanced when the sight window is disposed at angle with respect to the beam path, so that radiant energy directly reflected by the window surfaces, and independent of material moisture, will be directed away from the measurement unit. Thus window 32 is carried at an angle of fifty-five degrees with respect to the axis of tube 18. Furthermore, the inside surface of hollow sight tube 18 is preferably coated with light-absorptive material. Hence, only diffuse or scattered reflections from the material surface are received by the measurement head. The window angle of fifty-five degrees was empirically selected in accordance with the present invention to yield diffuse material reflection of sufficient intensity for measurement purposes, and yet insure that direct reflections are absorbed by the tube wall.

It has also been found that best results are obtained when the radiant energy is focused to the material/window interface. Thus, the length of sight tube 18 is preferably chosen to correspond with the particular head 72 with which it is to be used to place the beam focus at the desired location. This length is two hundred thirty (plus or minus twenty-five) millimeters in the case of the "Moisture Ray" head 72. For added support, a collar 76 is affixed to the case of head 72 and is slidably received over rod 58.

The sight tube and measuring head are assembled into a single unit, either at the factory or at the conveyor site. Opening 22 is then cut into chute 10 and the assembled unit is mounted thereto as described above. With sleeve 12, gasket 16, gland 20, flange 50 and rod 58 thus held in fixed position relative to chute 10, the position of window 32 and dam 49 may be adjusted relative to the material stream 79, which is depicted in broken lines in FIG. 3, by axially sliding tube 18 within gland 20 until the desired window/dam position is achieved. This may be carried out on a trial-and-error basis over a series of moisture measurements until an optimum window/dam position is located. Air conduit 28 is then connected to a selectively energizable source of compressed air, and the assembly is ready for operation.

Figure 4:
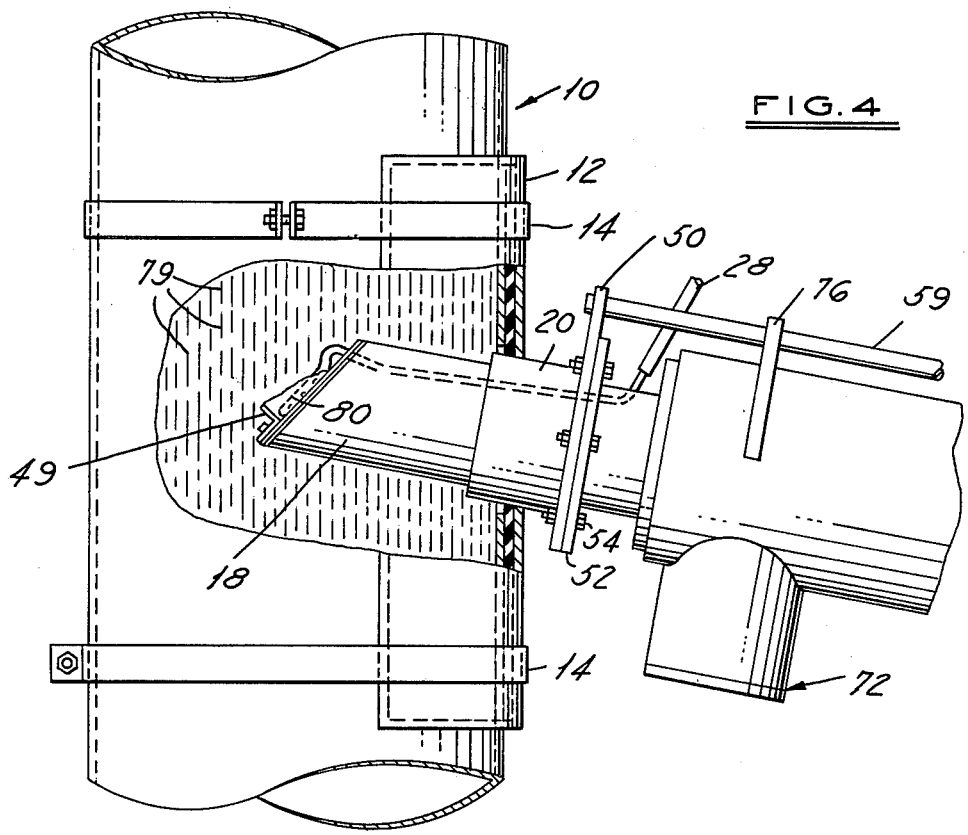
FIG. 4 is an elevational view similar to FIG. 1 showing the invention in operation.

When the sight tube is positioned in the material stream, dam 49 so restricts the flow of material over the window surface that a quantity of material is captured against the dam to form an inclined material pile 80 as depicted in FIG. 4. The deposit thus formed covers and is held by gravity against the outer surface of window 32. The amount of time required for such material build-up depends upon the rate and profile of material flow in the chute, and the adjusted position of the window and dam in the material stream. After a suitable period of time has been allowed for material deposition, the desired measurement may be taken as described above. When the measurement has been completed, a command is given to the compressed air source (not shown) to provide an air blast at nozzle 42 to blow the accumulated material from the surface of window 32 back into the material stream. System electronics should, of course, include suitable circuitry for holding the previous measurement and preventing initiation of a subsequent measurement while the sample is being removed and a new sample is being collected. When the air blast is terminated, the surface of window 32 is left clean and bare of material, whereupon a fresh material sample will automatically collect on the window and the measurement sequence may be repeated.

It will be apparent from the foregoing description that the described sight tube apparatus and sampling technique provided in accordance with the invention fully satisfies all of the objects and aims set forth above. For example, the entire process of material sampling and measurement may be accomplished automatically over an extended period of time without human intervention. Moreover, since there are no moving parts, and since the material sample is never physically removed from the bulk stream, many more measurements may be affected per unit time than with prior art techniques. Furthermore, it will be noted that sight tube 18 is sealed at both ends (at the outer end by window 62, and at the inner end by end plate 24 welded to the tube rim and by the cooperative relationship between window 32, sealing ring 38, window plate 34 and sealing ring 40 with end plate 24), and that the tube entrance and exit for air line 26 are sealed by welding. Thus, the measurement beam path provided by the hollow sight tube completely isolates the beam from the detrimental effects of ambient dust and/or humidity which could otherwise cause erroneous readings. The assembly may also be readily removed from chute 10 and disassembled for repair. Specifically, that part of the assembly most susceptible to wear or damage—i.e., window 32—may be quickly replaced by merely sliding tube 18 out of gland 20 and removing plate 34 via screws 36. A new window may be quickly inserted and the structure reassembled without significant apparatus downtime.

Although the invention has been described with reference to a specific embodiment thereof, many alternatives and modifications may be made without departing from the spirit and scope of the invention. For example, the fifty-five degree angle of window 32 with respect to the tube axis was empirically chosen, as described above, and may be changed as conditions dictate. Similarly, the ten degree angle of the tube axis with respect to the horizontal was chosen to minimize the required size of gland 20, but still yield a good window/material-flow angle, i.e., forty-five degrees. The disclosed embodiment may be modified, e.g. by provision of suitable folding mirrors within tube 18 and/or providing a steeper tube axis angle, to locate window 32 on a horizontal plane, and to thus eliminate the requirement for a separate dam 49. However, the relative cost and complexity of such a modification, including the obvious difficulties associated with accurately positioning the required reflecting surfaces within the sight tube, are considered to render such modification less preferable than that disclosed.

It is also possible, under proper circumstances, to eliminate dam 49 of the preferred embodiment, such that material moving in the bulk stream flows continually over the window surface. For proper performance of such a modification, the material flow would have to be constant and even; otherwise, a measurement may be attempted with an inadequate layer of material on the window, thereby yielding erroneous results. Hence, it is considered preferable to provide some means at the sight window for retarding material flow thereover, and to thereby insure that material will be present on the window when a measurement is to be made. Such means may comprise, for example, a frustum-shaped funnel in which the sight window is disposed in one funnel wall. However, the downstream funnel depth required for reliable operation would probably be such that the sight tube assembly would no longer be insertable through a relative small hole in the chute wall, as in the embodiment disclosed. Hence, for all of these reasons, the disclosed embodiment is preferred. However, the invention is intended to embrace the above-noted and all other alternatives, modifications and variations as fall within the spirit and broad scope of the appended claims.

The invention claimed is:

1. The method of measuring a characteristic of granular materials flowing generally downwardly in a bulk material stream comprising the steps of:
   (a) providing an optical window in a said flowing bulk material stream facing against the direction of travel of material in said stream at an angle transverse to the direction of travel of material in said stream,
   (b) accumulating and holding by force of gravity a stationary sample of said material on said window while the bulk of material continues to flow in said stream past said window and said stationary sample,
   (c) measuring said material characteristic by detecting at least one optical characteristic of said sample of material through said window while said material sample is stationarily held by gravity against said window in said continuously flowing material stream, and
   (d) removing said accumulated sample from said window after measurement of said material characteristic.

2. The method set forth in claim 1 wherein said steps (b) through (d) are repeated in periodic sequence to obtain sequential measurements of said material characteristic without substantially affecting the continuous flow of material in said stream.

3. The method set forth in claim 1 wherein said removing step (d) comprises the step of directing a stream of fluid across said window to remove said accumulated sample in their place.

4. The method set forth in claim 1 wherein said step (c) includes the steps of directing a light beam into said stationary material sample through said window from externally of said stream and detecting said optical characteristic as a function of a portion of said light beam reflected by said material sample back through said window.

5. A system for optically measuring a selected characteristic of granular material flowing vertically in a bulk material stream comprising means adapted to be disposed in said bulk material stream and including first surface means for providing an optical window through which said characteristic may be measured and second surface means disposed downstream of said first surface means adjacent thereto at an angle projecting into said material stream and in a direction opposed to flow of material such that a deposit of flowing material accumulates and is held stationary by gravity against said second means covering said window while the remainder of the flowing material in said bulk stream continues to flow past said first and second surface means, and means disposed externally of said material stream for detecting said material characteristic by directing a light beam through said window onto said material deposit and measuring reflections therefrom.

6. The system set forth in claim 5 further comprising means for removing an accumulated material deposit after said material characteristic has been measured.

7. In a system for optically measuring a selected characteristic of material flowing in a bulk material stream and including means for detecting said material characteristic by directing a light beam along a beam axis onto said material and measuring reflections therefrom, the improvement comprising an optical window disposed in said material stream and angulated with respect thereto such that material flowing in said stream contacts said window, a hollow sealed sight tube optically connecting said detecting means with said window and having a tube axis coincident with said beam axis with said window being disposed at one end of said tube at an acute angle with respect to said tube axis such that only diffuse reflections from said material are directed by said tube to said detecting means, said sealed tube isolating said beam and said reflections from the surrounding environment, means disposed adjacent said window to accumulate and hold stationary by the force of gravity a material sample on said window such that the bulk of material continues to flow in said stream past said window and said stationary sample, and means to remove an accumulated sample after said material characteristic has been measured.

8. The improvement set forth in claim 7 wherein said accumulating means comprises a dam carried downstream of said window and projecting into said material stream to block flow of material across said window.

9. The improvement set forth in claim 8 wherein said removing means comprises nozzle means disposed adjacent said window surface and means for connecting said nozzle to a source of compressed air.

10. The improvement set forth in claim 7 wherein said material stream is confined by a chute having a side wall and a chute axis, and wherein said window is spaced inwardly from said side wall into said material stream, said sight tube extending through said chute wall.

11. The improvement set forth in claim 10 further comprising means for adjustably mounting said window and sight tube to said chute wall such that said window may be adjustably positioned in said material stream.

12. The improvement set forth in claim 10 wherein said window is disposed at an angle of forty-five degrees with respect to said chute axis.

* * * * *